United States Patent [19]

Urbach

[11] 4,007,221
[45] Feb. 8, 1977

[54] MANUFACTURE OF NUCLEAR-IODINATED IODINE COMPOUNDS OF AROMATIC CHARACTER

[75] Inventor: Hans Urbach, Lampertheim, Germany

[73] Assignee: BASF Aktiengesellschaft, Ludwigshafen (Rhine), Germany

[22] Filed: Jan. 16, 1976

[21] Appl. No.: 649,580

[30] Foreign Application Priority Data

Jan. 29, 1975 Germany .......................... 2503504

[52] U.S. Cl. .................... 260/515 A; 260/290 HL; 260/310 R; 260/384; 260/505 R; 260/612 D; 260/649 R; 260/649 DP; 260/650 R; 260/646; 260/694

[51] Int. Cl.² ................. C07C 51/01; C07C 79/12; C07B 9/00

[58] Field of Search ........ 260/290 HL, 310 R, 384, 260/505 R, 515 A, 612 D, 649 R, 649 DP, 650 R, 646, 694

[56] References Cited

FOREIGN PATENTS OR APPLICATIONS 1,234,558   6/1971   United Kingdom ............... 260/694

Primary Examiner—Leland A. Sebastian
Attorney, Agent, or Firm—Johnston, Keil, Thompson & Shurtleff

[57] ABSTRACT

A process for the manufacture of nuclear-iodinated iodine compounds of aromatic character, by reaction of aromatic diazonium salts with hydriodic acid or its salts in aqueous solution in the presence of a reducing agent.

10 Claims, No Drawings

MANUFACTURE OF NUCLEAR-IODINATED IODINE COMPOUNDS OF AROMATIC CHARACTER

The present invention relates to a process for the manufacture of nuclear-iodinated iodine compounds of aromatic character by reaction of aromatic diazonium salts with hydriodic acid or its salts in aqueous solution in the presence of a reducing agent.

It has been disclosed that the reaction of aromatic diazonium salts with hydriodic acid or its salts leads to nuclear substitution by iodine (Ann. (1866) 137, 76). Chem. Ber. (1893) 26, 1744 describes exactly how this reaction is carried out when preparing o-iodobenzoic acid. According to this process, 1 mole of an aromatic primary amine is diazotized in dilute sulfuric acid solution and the diazonium solution thus obtained is allowed to run into a solution of 1.5 moles of potassium iodide in dilute sulfuric acid. The yield is almost quantitative.

Using this process, elementary iodine is formed during the addition of the diazonium solution, and escapes as a vapor which is precipitated in the reflux condenser. In addition, nitrous gases are evolved. The o-iodobenzoic acid which has been prepared by this process and isolated by filtration has a dark brown color, which can only be lightened slightly by washing with aqueous sodium bisulfite solution. On prolonged standing, the turbid and dark brown filtrate deposits a sediment.

These disadvantages substantially interfere with employing the above procedure industrially, for the following reasons:

The iodine deposited significantly reduces the efficiency of the condenser, so that the coolant throughput must be increased. Cleaning the condenser is troublesome and the iodine vapors formed during cleaning are extremely injurious to health.

The emission of iodine vapors and nitrous gases into the atmosphere is not permitted and must therefore be prevented by suitable measures. Sodium hydroxide solution can be used to absorb both iodine vapors and nitrous gases; however, the resulting absorption liquor can only be re-used to a limited extent, because of its iodine content.

The production of elementary iodine cannot be prevented by destroying excess nitrous acid in the diazonium solution, since the elementary iodine is also formed by decomposition of the diazonium salt to free radicals, and their reaction with the iodide.

A further disadvantage of the process is that an excess of 0.5 mole of iodide is required to achieve quantitative conversion. The iodide, or the triiodide produced from iodide and elementary iodine, which after the reaction is in the main present in the waste water, must be recovered by working up the latter. This requires additional investment and increases the operating costs.

We have found that these difficulties encountered in the industrial-scale manufacture of aromatic iodine compounds can be avoided by carrying out the reaction in the presence of a reducing agent which, under the particular conditions used, reduces elementary iodine to hydrogen iodide. Using this method, neither iodine vapors nor nitrous gases are formed. The yield is almost quantitative. This is surprising and was unforeseeable since the literature discloses processes wherein the yield of the reaction of aromatic diazonium salts with iodides is substantially improved by adding elementary iodine (Houben-Weyl, Methoden der organischen Chemie, volume 5/4 (1960), page 641).

The most essential advantage of the process according to the invention is that the amount of iodide can be reduced to the stoichiometric amount, i.e. 1 mole of hydriodic acid or 1 mole of iodide per mole of primary aromatic amine, without thereby reducing the yield. Accordingly, the waste water is free from elementary iodine and iodide. After isolating the reaction product, a clear pale yellow solution is obtained; working up of the waste water is superfluous.

A further economic advantage of the process is that any excess nitrite which may be present does not have to be destroyed in a separate process stage.

The reducing agents used can be all compounds and elements which, under the particular conditions, reduce elementary iodine to hydrogen iodide. Substances which, in the oxidized form, can be worked up easily and do not constitute a contaminant in the waste water, are particularly suitable. Preferred reducing agents are sulfur dioxide, neutral and acid salts of sulfurous acid, salts of thiosulfuric acid, e.g. sodium thiosulfate, salts of dithionous acids, e.g. sodium dithionite, sulfinic acids and salts of sulfinic acids, e.g. sodium hydroxymethylsulfinate.

Sulfur dioxide and sodium bisulfite are particularly suitable reducing agents, since these compounds are inexpensive and are converted, by oxidation, into sulfuric acid or sodium sulfate, which neither interfere with the isolation of o-iodobenzoic acid nor increase the contamination of the waste water.

It is possible for the reducing agent to be present initially, together with the iodide, as an aqueous solution, or to be added gradually, simultaneously with the diazonium solution. Equally, it is possible first to take the diazonium solution and to add the iodide solution, the reducing agent being contained in one of the two solutions.

The reducing agent in practice with generally be added in sufficient amount to decolorize the solution which is colored as a result of the formation of iodine.

The amount of reducing agent depends on the reaction conditions. If, e.g., a relatively large excess of nitrite or nitrous acid is used in the diazonium solution, more reducing agent is required than if the stoichiometric amount of nitrite is used. If the excess nitrous acid is destroyed before the reaction with iodide by adding urea or amidosulfonic acid, the amount of reducing agent required is reduced accordingly. If, for example, equimolar amounts of primary aromatic amine, nitrite and iodide are used, from about 0.05 to 0.1 mole of sulfur dioxide or sodium bisulfite is required per mole of iodide. The amount of reducing agent should be kept as low as possible.

Suitably, just sufficient reducing agent is added that the solution which is colored due to the formation of iodine is again decolorized. The consumption of reducing agent during the reaction can be checked not only visually but also amperometrically, most suitably by the dead stop method.

Suitable starting materials are compounds of aromatic character, which can be diazotized in the conventional manner with nitrite in an acid medium, preferably primary, optionally nuclear-substituted, mononuclear, or fused or non-fused poly-nuclear, aromatic amines, e.g. anthranilic acid, p-aminobenzoic acid, 1-methyl-2-amino-4-nitrobenzene, 2-amino-4-nitroanisole, 3-amino-4,6-dinitro-anisole, 4-amino-6- nitrotoluene-3-sulfonic acid, 2-amino-biphenyl, 2-amino-naphthalene, 2-amino-anthraquinone and 9-amino-phenanthrene. Heterocyclic compounds of aromatic character, which carry at least one amino group, can also be used, e.g. 3-amino-2-hydroxy-pyridine, 5-amino-2-hydroxypyridine and 4-amino-1,3,5-trimethyl-pyrazole.

Hydriodic acid and its salts, preferably potassium iodide, may be used as the agents which act as sources of iodide.

The reaction of the diazonium solution with the iodide solution may be carried out at from 0° to 100° C, preferably from 20° to 50° C. If low reaction temperatures are used, the mixture is subsequently heated to from 80° to 100° C, if required.

The reaction time is substantially shorter than in the conventional processes. Whilst in these several hours' heating at the boil was required to achieve a quantitative yield, it suffices, in the process according to the invention, if the reactants are stirred, after mixing, for up to 1 hour, if appropriate at an elevated temperature.

The Examples which follow illustrate the manufacture of aromatic iodine compounds by the process of the invention.

EXAMPLE 1

Preparation of o-iodobenzoic acid 153 parts by weight of concentrated sulfuric acid and 137 parts by weight of anthranilic acid are introduced successively into 500 parts by weight of water in a stirred vessel. A solution of 69 parts by weight of sodium nitrite in 100 parts by weight of water is added to the resulting suspension in the course of about 20 minutes at from 0° to 5° C. The mixture is then stirred for a further 30 minutes at from 0° to 10° C. In another stirred vessel, 166 parts by weight of potassium iodide are dissolved in 375 parts by weight of water and 66 parts by weight of concentrated sulfuric acid and 25 parts by weight of a 40% strength aqueous sodium bisulfite solution are added successively. The diazonium solution is allowed to run into this solution in the course of about 30 minutes, with external cooling, the temperature being kept at from 20° to 40° C. The mixture is then stirred for 30 minutes at about 40° C, after which it is heated at from 70° to 80° C for one hour. After cooling, filtering on a suction filter and washing with 40 parts by weight of water, 242 parts by weight of o-iodobenzoic acid are obtained. Melting point = 160°–162° C. Yield 97% of theory.

If the reaction is repeated in the absence of a reducing agent, a blackish brown o-iodobenzoic acid of melting point 145°–150° C is obtained in only 75% yield. During the reaction, iodine vapors form and these partly deposit in the condenser and partly escape from the reactor with the nitrous gases which are also formed. After completion of the reaction, resinous deposits were found on the walls of the stirred vessel.

o-Iodobenzoic acid is an intermediate for the manufacture of fungicides. For example, reaction of o-iodobenzoic acid with aniline gives o-iodobenzanilide, which has a good fungicidal action when used in plant protection.

EXAMPLE 2

Preparation of iodobenzene

A phenyldiazonium sulfate solution prepared from 93 parts by weight of aniline, 153 parts by weight of concentrated sulfuric acid, 600 parts by weight of water and 69 parts by weight of sodium nitrite is run in the course of 30 minutes, at 40° C, into a solution of 375 parts by weight of water, 66 parts by weight of concentrated sulfuric acid, 166 parts by weight of potassium iodide and 75 parts by weight of an aqueous 40% strength sodium bisulfite solution, the latter only being added just before the diazonium salt solution is run in. The mixture is stirred for 30 minutes at 40° C and then for 60 minutes at from 75° to 80° C, after which it is cooled to from 20° to 30° C. The iodobenzene is removed from the aqueous phase by extraction with 200 parts by weight of benzene. Distillation under reduced pressure gives first runnings of benzene, followed by 167 parts by weight of iodobenzene, of boiling point 67° C/12 mm Hg. Yield 85% of theory.

If the batch is run without an added reducing agent, sticky by-products form on the walls of the reaction vessel and after distillation a blackish red turbid liquid smelling of phenol is obtained.

EXAMPLE 3

Preparation of o-nitroiodobenzene

A solution of 69 parts by weight of o-nitroaniline in 250 parts by weight of water and 76.5 parts by weight of concentrated sulfuric acid is diazotized in the course of 30 minutes with a solution of 35 parts by weight of sodium nitrite in 50 parts by weight of water at from 0° to 10° C. This diazonium salt solution is run, in the course of 30 minutes, into a solution of 188 parts by weight of water, 33 parts by weight of concentrated sulfuric acid, 83 parts by weight of potassium iodide and 12.5 parts by weight of a 40% strength aqueous sodium bisulfite solution, the latter only being added shortly before starting to add the diazonium salt solution. The temperature is kept at 20° C by cooling and stirring is continued for one hour at this temperature. On filtration, 122 parts by weight of a yellowish brown finely granular crystalline product, melting at 49° C after drying, are obtained. Yield 98% of theory.

If the batch is run without an added reducing agent, a sticky blackish brown product with an intense odor of phenol is obtained in 95% yield; melting point 41° C. In addition, the condenser of the apparatus is colored red due to condensed iodine.

EXAMPLE 4

Preparation of 2-iodonaphthalene 100 parts by weight of 2-amino-naphthalene, in a mixture of 4,000 parts by weight of water and 113 parts by weight of concentrated hydrochloric acid, are diazotized with a solution of 50 parts by weight of sodium nitrite in 50 parts by weight of water. The diazonium solution thus prepared is run, in the course of 30 minutes at 35°–40° C, into a solution of 36 parts by weight of concentrated sulfuric acid and 116 parts by weight of potassium iodide in 200 parts by weight of water. During the addition of the diazonium solution, a 40% strength aqueous sodium bisulfite solution is added gradually to ensure that no elementary iodine is produced. 40 parts by weight of the reducing solution are consumed.

After stirring for a further hour at 40° C, the solid product is filtered off. After drying, 172 parts by weight of dark-colored crystals of melting point 45°–48° C are obtained.

On repeating the experiment without added sodium bisulfite, only 158 g of crystalline product are obtained.

I claim:

1. In a process for the manufacture of an aromatic nuclear-iodinated iodine compound by reacting an aromatic diazonium salt with hydriodic acid or a salt thereof, the improvement which comprises carrying out the reaction in aqueous solution and in the presence of a reducing agent.

2. A process as claimed in claim 1 which includes the steps of diazotizing an aromatic compound in an acid medium to provide said diazonium salt in solution and then adding the resulting diazonium solution to an aqueous solution containing the hydriodic acid or a salt thereof and the reducing agent.

3. A process as claimed in claim 1 wherein the reducing agent is sulfur dioxide or a neutral or acid salt of sulfurous acid.

4. A process as claimed in claim 1 wherein the reducing agent is added in sufficient amount to decolorize the solution, which is colored due to the formation of iodine.

5. The process of claim 2 wherein anthranilic acid is diazotized and reacted to produce o-iodobenzoic acid.

6. The process of claim 2 wherein o-nitroaniline is diazotized and reacted to produce o-nitroiodobenzene.

7. The process of claim 1 wherein the hydroiodic acid or its salt is reacted in about the stoichiometric amount required for reaction with the aromatic diazonium salt.

8. The process of claim 1 wherein the aromatic diazonium salt is the sulfate.

9. The process of claim 1 wherein the aromatic diazonium salt is reacted with potassium iodide in approximately the stoichiometric amount.

10. The process of claim 9 wherein the reducing agent is sulfur dioxide or a neutral or acid salt of sulfurous acid.

* * * * *